US008062626B2

(12) United States Patent
Freund et al.

(10) Patent No.: US 8,062,626 B2
(45) **Date of Patent: *Nov. 22, 2011**

(54) STABLE PHARMACEUTICAL BUDESONIDE PREPARATION FOR PRODUCING PROPELLANT-FREE AEROSOLS

(75) Inventors: Bernhard Freund, Gau-Algesheim (DE); Michael Krueger, Ingelheim (DE); Bernd Zierenberg, Bingen (DE)

(73) Assignee: Boehringer Ingelheim KG, Ingelheim am Rhein (DE)

( * ) Notice: Subject to any disclaimer, the term of this patent is extended or adjusted under 35 U.S.C. 154(b) by 734 days.

This patent is subject to a terminal disclaimer.

(21) Appl. No.: 11/968,903

(22) Filed: Jan. 3, 2008

(65) Prior Publication Data

US 2008/0102037 A1 May 1, 2008

Related U.S. Application Data

(63) Continuation of application No. 11/351,095, filed on Feb. 9, 2006, now abandoned, which is a continuation of application No. 10/373,515, filed on Feb. 25, 2003, now abandoned, which is a continuation of application No. 10/102,495, filed on Mar. 20, 2002, now abandoned, which is a continuation of application No. 09/396,673, filed on Sep. 9, 1999, now Pat. No. 6,491,897, which is a continuation of application No. 08/973,921, filed as application No. PCT/EP96/02700 on Jun. 21, 1996, now abandoned.

(30) Foreign Application Priority Data

Jun. 27, 1995 (DE) ................................. 195 23 207

(51) Int. Cl.
*A61K 9/12* (2006.01)
*A61K 9/14* (2006.01)
*A61M 11/00* (2006.01)

(52) U.S. Cl. ........................ 424/45; 424/46; 128/200.14

(58) Field of Classification Search .................... 424/45, 424/46; 128/200.14

See application file for complete search history.

(56) References Cited

U.S. PATENT DOCUMENTS

| | | | |
|---|---|---|---|
| 4,289,764 | A | 9/1981 | Yarrow |
| 4,383,992 | A | 5/1983 | Lipari |
| 4,450,151 | A | 5/1984 | Shinozawa |
| 4,615,699 | A | 10/1986 | Gale et al. |
| 4,857,312 | A | 8/1989 | Hegasy et al. |
| 4,919,919 | A | 4/1990 | Aouda et al. |
| 5,047,230 | A | 9/1991 | Nagy et al. |
| 5,136,124 | A | 8/1992 | Cronin et al. |
| 5,225,183 | A | 7/1993 | Purewal et al. |
| 5,370,862 | A | 12/1994 | Klokkers-Bethke et al. |
| 5,474,759 | A | 12/1995 | Fassberg et al. |
| 5,674,471 | A | 10/1997 | Akehurst et al. |
| 5,736,124 | A | 4/1998 | Akehurst et al. |
| 5,776,432 | A | 7/1998 | Schultz et al. |
| 5,914,122 | A | 6/1999 | Otterbeck et al. |
| 5,958,378 | A | 9/1999 | Waldrep et al. |
| 6,004,537 | A | 12/1999 | Blondino et al. |
| 6,039,932 | A | 3/2000 | Govind et al. |
| 6,491,897 | B1 | 12/2002 | Freund et al. |
| 6,890,517 | B2 | 5/2005 | Drechsel et al. |

FOREIGN PATENT DOCUMENTS

| | | | |
|---|---|---|---|
| DE | 3246081 | | 6/1984 |
| DE | 195 23 207 | | 1/1986 |
| DE | 4123663 | | 1/1993 |
| DE | 44 46 891.1 | | 7/1996 |
| EP | 0234 500 | A1 | 9/1987 |
| EP | 0310910 | | 4/1989 |
| EP | 0468555 | | 1/1992 |
| EP | 0504112 | | 9/1992 |
| EP | 0605578 | B1 | 7/1994 |
| GB | 970027 | | 9/1964 |
| GB | 1525181 | * | 9/1978 |
| WO | 82/03172 | | 9/1982 |
| WO | 90/06750 | A1 | 6/1990 |
| WO | 92/06675 | A1 | 4/1992 |
| WO | 93/05765 | A1 | 4/1993 |
| WO | 93/15715 | A1 | 8/1993 |
| WO | 93/15741 | A1 | 8/1993 |
| WO | 94/13262 | A1 | 6/1994 |
| WO | 95/14474 | A1 | 6/1995 |
| WO | 96/19969 | A1 | 7/1996 |
| WO | 97/01329 | A1 | 1/1997 |

OTHER PUBLICATIONS

C. Monder, Stability of Corticosteroids in Aqueous Solutions, Endocrinology, vol. 82, 1968, pp. 318-326.
M. Nyman-Pantelidis et al., Pharmacokinetics and retrograde colonic spread of budesonide enemas in patients with distal ulcerative colitis, Alimentary Pharmacology & Therapeutics, Bol. 8, 1994, pp. 617-622.
Declaration by Hans Nilsson regarding the matter of European Patent No. 0 794 767-regarding the manufacture and public availability of Rhinocort Aqua: before 1994, In the name of Dr. Falk Pharma GmbH and Opposition thereto by Astra AB.
Declaration by Anders Akerlund, regarding the matter of European Patent No. 0 794 767-regarding the public availability of Rhinocort Aqua: before 1994, In the name of Dr. Falk Pharma GmbH and Opposition thereto by Astra AB.
Monograph Entocort, Oxford Clinical Communications 1992, First Update and Reprint 1995. Title page and page 1 from Laekartidningen, vol. 22, 1987.
Letter from "Laekemedelsverket" regarding public availability and the date of publication of the Composition of "Rhinocort Aqua" before Jun. 13, 1986.
Patent Abstracts of Japan, vol. 5, No. 136 [808], Aug. 28, 1981; & JP-56071046 A (Nippon Kayaku K.K.) Jun. 13, 1981.
Chem. Abstract, vol. 10 No. 252 JP 61-83117 (A) Apr. 26, 1986.
Dahlbaeck, M, et al, Inhalation of Glucocorticoid Particles (GCS) (Budesonide) to the Rat Lung, to Prevent Lung Edema Formation, J. Aerosols in Science, Medicine and Technology (1984) vol. 15, No. 3, 0. 218-219.
Williams S.J., et al, Bronchodilator effect of Deltal-tetrahydrocannabinol administered by aerosol to asthmatic patents. Thorax (1976), vol. 31, No. 6 pp. 720-723.

(Continued)

*Primary Examiner* — Mina Haghighatian

(74) *Attorney, Agent, or Firm* — Michael P. Morris; Mary-Ellen M. Devlin

(57) ABSTRACT

The invention relates to ethanol-containing pharmaceutical preparations for the production of propellant-free aerosols.

15 Claims, No Drawings

OTHER PUBLICATIONS

Davis, S.S., et al, Physico-Chemical Studies on Aerosol Solutions for Drug Delivery II. Water-Propylene Glycol-Ethanol Systems. Int. J. of Pharmaceutics, (1978) vol. 1, No. 2, pp. 85-93.

Timmins and Gray, The degradation of triamcinolone acetonide in aqueous solution: influence of the cyclic ketal function. J. Pharm. Pharmacol, 1983, vol. 35, pp. 175-177.

Das Gupta, V., Stability of Triamcinolone Acetonide Solutions as Determined by High-Performance Liquid Chromatography. (1983), vol. 72, No. 12, pp. 1453-1456.

Derbacher & Zimmermann, Physikalische Eigenschaften von Inhalationsloesungen. Atemwegs und Lungenkrankheiten, 1994, vol. 20 No. 7, pp. 381-382.

Hansen & Bundgaard, Studies on the stability of corticosteroids. Arch. Pharm Chemi. Sci. Ed. 7, 1979, pp. 135-146.

H. Nolen III, et al., Budesonide-Beta-D-glucuronide: A Potential Prodrug for Treatment of Ulcerative Colitis. J. Pharm. Sci., 1995, vol. 84, No. 6 pp. 677-681.

C. Lamers, et al., Comparative study of the topically acting glucocorticosteroid budesonide and 5-aminosalicylic acid enema therapy of proctitis and proctosigmoiditis. Gastroenterology 1991, 100, A223.

A. Danielsson, et al., A Controlled Randomized Trial of Budesonide versus Prednisolone Retention Enemas in Active Distal Ulcerative Colitis. Scand. J. Gastroenterol., 1987 vol. 22 pp. 987-992.

The Danish Budesonide Study Group, "Budesonide Enema in Distal Ulcerative Colitis". Scand. J. Gastroenterol., 1991, vol. 26, pp. 1225-1230.

G. B. Porro, et al., "Comparative trial of methylprednisolone and budesonide enemas in active distal ulcerative colitis". Eur. J. Gastroenterol., 1994, vol. 6, pp. 125-130.

Advertisement in Laekartidningen, No. 22/87 dated May 27, 1987 for Rhinocort(R) Aqua and English translation thereof.

"The official document for the Composition Data for Rhinocort(R)" aqua dated Mar. 5, 1987 and English translation thereof.

N. Linnet, "pH Measurements in Theory and Practice". Radiometer A/S, Copenhagen 1970, pp. 94-96.

"L'Informatatore Farmaceutico", Annuario Italiano Dei Medicamenti E Dei Laboratori Italian Directory of Drugs and Manufactures, 1993, vol. 1, 53rd edition, p. 105.

Dekker & Beijnen, "Effects of Substituents in Dihydroxy-acetone Side chain Containing Corticosteroids on the Anerobic Steroid Decomposition." Pharm. Acta Helv. 1982, vol. 57, No. 1, pp. 4-7.

D. M. Johnson, "Degradation of Cloprendol in Aqueous Solution. The Enolization Step," J. Org. Chem., 1982 vol. 47, pp. 198-201.

Hansen & Bundgaard "Studies on the stability of corticosteroids v. the degradation pattern of hydrocortisone in aqueous solution", pp. 307-319, 1980.

Amin & Bryan, "Kinetics and Factors Affecting Stability of Methylprednisolone in Aqueous Formulation," Journal of Pharmaceutical Sciences, No. 1973, vol. 62, No. 11, pp. 1768-1771.

\* cited by examiner

STABLE PHARMACEUTICAL BUDESONIDE PREPARATION FOR PRODUCING PROPELLANT-FREE AEROSOLS

The present invention relates to pharmaceutical preparations in the form of stable ethanolic solutions of active substances for producing propellant-free aerosols.

In the last 20 years, the use of metering aerosols has become an established component of the treatment of obstructive lung diseases, particularly asthma. Usually, fluorochlorohydrocarbons have been used as propellant gases. Since the ozone-damaging potential of these propellant gases was recognised, more and more efforts have been made to develop alternatives. One alternative is the development of nebulisers in which aqueous solutions of pharmacologically-active substances are sprayed under high pressure so as to produce a mist of inhalable particles. The advantage of these nebulisers is that there is no need to use any propellant gases whatsoever.

Some nebulisers are described, for example, in PCT Patent Application WO91/14468, the contents of which are referred to hereinafter. In the nebulisers described therein, solutions of defined volumes containing active substances are sprayed, using high pressures through small nozzles so as to produce inhalable aerosols with a preferred particle size of between 1 and 10, preferably between 2 and 5 micrometers.

Hitherto, it has been assumed that, with conventional metering aerosols containing propellant gas, the optimum level of lung-bound particles is obtained in the aerosol. It has now been found, surprisingly, that by using ethanolic active substance solutions in combination with, for example, the above-mentioned nebulisers it is possible to generate a significantly better spectrum of inhalable particles than is usually the case with metering aerosols which contain propellant gas.

Suitable solvents for the pharmaceutical preparation within the scope of the present inventions are solutions containing at least 70% (v/v) of ethanol; solutions containing at least 85% (v/v) are preferred whilst solutions having an ethanol content of more than 95% (v/v) are particularly preferred. The concentration is given in percent by volume (v/v), the remainder being water. Most particularly preferred is ethanol which already contains small amounts of water, e.g. 96% ethanol, so that it is no longer hygroscopic and evaporates azeotropically.

Apart from water, the solvent may include other cosolvents and the pharmaceutical preparation may also contain flavourings and other pharmacological excipients. Examples of cosolvents are those which contain hydroxyl groups or other polar groups, e.g. alcohols, especially isopropyl alcohol, glycols, particularly propylene glycol, polyethylene glycol, polypropylene glycol, glycol ether, glycerol, polyoxyethylene alcohols and esters of polyoxyethylene fatty acids. Cosolvents are suitable for increasing the solubility of the excipients and possibly the active substances.

The proportion of dissolved pharmaceutical substance in the finished pharmaceutical preparation is between 0.001 and 5%, preferably between 0.05 and 3%, most particularly 0.01 to 2%, where the figures refer to the percentage by weight. The maximum concentration of pharmaceutical substance depends on the solubility in the solvent and on the dosage required to achieve the desired therapeutic effect.

As pharmaceutically active agent in the new preparations, it is possible to use any substances which are suitable for administration by inhalation and which are soluble in the solvent specified. These may include, in particular, betamimetics, anticholinergics, antiallergics, PAF-antagonists and particularly steroids and combinations of active substances thereof.

The following are mentioned specifically by way of example:
Tiotropium bromide, 3-[(hydroxydi-2-thienylacetyl)oxy]-8,8-dimethyl-8-azoniabicyclo[3,2,1]oct-6-en-bromide As betamimetics:

| Bambuterol | Bitolterol | Carbuterol | Formoterol |
|---|---|---|---|
| Clenbuterol | Fenoterol | Hexoprenaline | Procaterol |
| Ibuterol | Pirbuterol | Salmeterol | Tulobuterol |
| Reproterol | Salbutamol | Sulfonterol | Terbutaline |

1-(2-fluoro-4-hydroxyphenyl)-2-[4-(1-benzimidazolyl)-2-methyl-2-butylamino]ethanol,
erythro-5'-hydroxy-8'-(1-hydroxy-2-isopropylaminobutyl)-2H-1,4-benzoxazin-3-(4H)-one,
1-(4-amino-3-chloro-5-trifluoromethylphenyl)-2-tert.-butyl-amino)ethanol,
1-(4-ethoxycarbonylamino-3-cyano-5-fluorophenyl)-2-(tert.-butylamino)ethanol.

As anticholinergics:
Ipratropium bromide
Oxitropium bromide
Trospium chloride
N-β-fluorethylnortropine benzilate methobromide As steroids:
Budesonide;
Beclomethasone (or the 17,21-dipropionate)
Dexamethasone-21-isonicotinate
Flunisolide As antiallergics:
Disodium cromoglycate
Nedocromil
Epinastin As PAF-antagonists:
WEB 2086 (4-(2-chlorophenyl)-9-methyl-2-[3-(4-morpholinyl)-3-propanon-1-yl]-6H-thieno-[3,2-f][1,2,4]-triazolo [4,3-a][1,4]diazepine)
WEB 2170 (6-(2-chlorophenyl)-8,9-dihydro-1-methyl-8-[(4-morpholinyl)carbonyl]-4H,7H-cyclopenta[4,5]thieno-[3,2-f][1,2,4]triazolo[4,3-a][1,4]diazepine)

The pharmaceutical preparations according to the invention may contain other excipients such as soya lecithin or surface-active substances.

Surprisingly, it has also been found that the addition of an organic or inorganic acid, preferably in conjunction with a complex forming agent, leads to an improvement in the stability (shelf life) of steroid-containing preparations. This has been found particularly useful for pharmaceutical preparations which contain as active substance Flunisolide or the hydrate or hemihydrate thereof or Budenoside, and which contain ethanol as solvent.

Examples of inorganic acids include, for example: hydrochloric acid, sulphuric acid or phosphoric acid; examples of organic acids include ascorbic acid, malic acid, citric acid, tartaric acid, maleic acid, succinic acid, fumaric acid, acetic acid, formic acid, propionic acid, etc.

The amount of acid in the finished pharmaceutical preparation is in every case selected so that the pH of the solution is between 2.0 and 7.0, especially between 3.0 and 4.0.

In a preferred embodiment, the pharmaceutical preparation also contains a complex forming agent. Examples of complex forming agents include EDTA, citric acid, nitrilo triacetic acid and the salts thereof. The quantity of complex forming agent is between 0.1 and 3 mg/100 ml, preferably between 0.2 and 2 mg/100 ml, particularly between 0.9 and 1.1 mg/100 ml, based on the finished pharmaceutical preparation.

The preferred complex forming agent is EDTA (ethylene diamine tetraacetic acid or a salt thereof, such as the disodium salt). A preferred pharmaceutical preparation according to the present invention contains 1.667% Flunisolide in the ethanol (96% v/v) as solvent, which contains 0.01% (v/v) EDTA as complex forming agent and is adjusted by the addition of acid to a pH of between 3.0 and 4.0.

Examples of steroids which may be used as an active substance in the pharmaceutical preparation according to the invention are:

| | |
|---|---|
| Seratrodast | Mycophenolate mofetil |
| Pranlukast | Zileuton |
| Butixocort | Budesonide |
| Deflazacort | |
| Fluticasone | Promedrol |
| Mometasone furoate | Tipredane |
| Beclomethasone, Douglas | Icomethasone enbutate |
| Ciclometasone | Cloprednol |
| Fluocortin butyl | Halometasone |
| Deflazacort | Alclometasone |
| Ciclometasone | Alisactide |
| Prednicarbate | Hydrocortisone butyrate |
| Tixocortol pivalate | Alclometasone dipropionate |
| Lotrisone | Canesten-HC |
| Deprodone | Fluticasone propionate |
| Methylprednisolone-Aceponate | Halopredone acetate |
| Mometasone | Mometasone furoate |
| Hydrocortisone aceponate | Mometasone |
| Ulobetasol propionate | Aminoglutethimide |
| Triamcinolone | Hydrocortisone |
| Meprednisone | Fluorometholone |
| Dexamethasone | Betamethasone |
| Medrysone | Fluclorolone acetonide |
| Fluocinolone acetonide | Paramethasone acetate |
| Deprodone Propionate | Aristocort diacetate |
| Fluocinonide | Mazipredone |
| Difluprednate | Betamethasone valerate |
| Dexamethasonisonicotinate | Beclomethasone dipropionate |
| Fluocortoloncapronate | Formocortal |
| Triamcinolon hexacetonide | Cloprednol |
| Formebolone | Clobetason |
| Endrisone | Flunisolide |
| Halcinonide | Fluazacort |
| Clobetasol | Hydrocortisone-17-butyrate |
| Diflorasone | Flucortin |
| Amcinonide | Betamethasone dipropionate |
| Cortivazol | Betamethasone adamantoate |
| Fluodexan | Triiostane |
| Budesonide | Clobetasone |
| Demetex | Trimacinolon Benetonide |

9α-chloro-6α-fluoro-11β,17α-dihydroxy-16α-methyl-3-oxo-1,4-androstadiene-17β-carboxylic acid methylester-17-propionate.

Table 1 shows a comparison of a deposition study which was carried out on the one hand with a standard commercial metering aerosol Inhacort® (Flunisolide, dichloromethane, trichlorofluoromethane, cryofluoran, sorbitane triolate)= MDI, and on the other hand with the pharmaceutical preparation according to the invention containing Flunisolide in 96% (v/v) ethanol, which was carried out with a nebuliser as in the above-mentioned PCT Application WO 91/14468 (BINEB®; technical data: volume of drug preparation administered 15 μl, pressure approx. 300 bar, 2 jets squeezed out of two nozzle openings measuring 5×8 μm).

TABLE 1

Table 1: Deposition study

| | BINEB ® | MDI |
|---|---|---|
| Lung (%) | 39.7 (9.9) | 15.3 (5.1) |
| Mouthpiece (%) | 39.9 (9.4) | 66.9 (7.1) |
| Exhaled part (%) | 10.4 (4.9) | 1.4 (1.3) |
| Central lung region (%) | 10.7 (2.5) | 4.5 (1.8) |
| Middle lung region (%) | 14.9 (3.6) | 5.4 (1.9) |
| Peripheral lung region (%) | 14.1 (4.3) | 5.4 (1.4) |
| Peripheral zone/central zone ratio | 1.3 (0.2) | 1.3 (0.2) |

The Table clearly shows the advantage of the pharmaceutical preparation according to the invention which was administered with the nebuliser described.

EXAMPLES

Flunisolide hemihydrate-6α-fluoro-11β,16α,17α,21-tetrahydropregna-1,4-diene-3,20-16 acetonide hemihydrate has a molecular weight of 442.5. When used in BINEB, 250 μg of Flunisolide are dissolved, per dose, in 15 μl of solution so as to give a concentration of 1.667% (g/100 ml).

96% ethanol is used as solvent. In addition, the finished pharmaceutical preparation contains 1 mg/100 ml of disodium-EDTA. The pH value of the pharmaceutical preparation is adjusted to pH 4 using 0.1N HCl.

Analogously to the above experiment, formulations were prepared containing Budesonide as active substance.

The following mixtures of pharmaceutical preparations were made up, containing Flunisolide-hemihydrate as active substance.

TABLE II

| Experiment No. | Combination | Ethanol content (v/v) % | pH | Quantity of disodium EDTA in mg/100 ml |
|---|---|---|---|---|
| 1 | 1 | 85 | 3.6 | 0 |
| 2 | A | 96 | 3.6 | 0 |
| 3 | B | 85 | 7.0 | 0 |
| 4 | AB | 96 | 7.0 | 0 |
| 5 | C | 85 | 3.6 | 1 |
| 6 | AC | 96 | 3.6 | 1 |
| 7 | BC | 85 | 7.0 | 1 |
| 8 | ABC | 96 | 7.0 | 1 |

The Flunisolide-hemihydrate content was 1,666.7 mg/100 ml. The pH of the solution was adjusted using 1N HCl and was determined using a pH meter, pH 1162 Radiometer Copenhagen. The samples were transferred into 5 ml glass ampoules and stored at 80° C. away from light. The combination AC showed the lowest amount of decomposition product after 30 days' storage.

Further examples of formulations which additionally contain disodium EDTA as complex forming agent are shown in Table III.

TABLE III

| Ingredients | I Amount in mg/100 ml | II Amount in mg/100 ml | III Amount in mg/100 ml | IV Amount in mg/100 ml |
|---|---|---|---|---|
| Flunisolide hemihydrate | 1667 | 1667 | 1667 | 1667 |
| Disodium EDTA | 1 | 1 | 1 | 1 |
| 0.1N HCl | ad pH 3.6 | ad pH 3.2 | ad pH 4.0 | ad pH 3.6 |
| Menthol | — | — | — | 667 |
| Ethanol 96% | ad 100 ml | ad 100 ml | ad 100 ml | ad 100 ml |

The adjuvant menthol was added in order to mask the bitter flavour of the steroid where necessary.

The formulations described above were packaged in 5 ml glass ampoules and stored at 80° C. The preferred preparation, on account of the small amount of decomposition product, is preparation III.

Table IV shows some examples of formulations for Budenoside.

TABLE IV

| Ingredients | I Amount in mg/100 ml | II Amount in mg/100 ml | III Amount in mg/100 ml | IV Amount in mg/100 ml | V Amount in mg/100 ml |
| --- | --- | --- | --- | --- | --- |
| Budesonide | 1333 | 1333 | 1333 | 1333 | 1333 |
| Disodium EDTA | 1 | — | 1 | 1 | — |
| 0.1N HCl ad pH | 3.2 | 3.2 | 3.6 | 4.0 | 4.0 |
| Ethanol 96% ad | 100 | 100 | 100 | 100 | 100 |

After 3 months' storage at 80° C. in sealed glass ampoules the amount of decomposition product was determined by HPLC. Formulations IV and V showed the smallest amount of decomposition product.

The invention claimed is:

1. A stable pharmaceutical preparation for use in producing propellant-free aerosols which comprises a pharmacologically active substance, and if necessary, pharmacologically-harmless adjuvants and/or flavourings, characterised in that the pharmaceutical preparation contains at least 70% (v/v) ethanol as a solvent with a pH between 2.0 and 7.0 wherein
   said active substance is selected from the group consisting of betamimetics, anticholinergics, antiallergics, PAF-antagonists, steroids and combinations of said active substances in amounts of 0.001 to 5.0% by weight
   and said pharmaceutical preparation is administered with a nebulizer which nebulises the preparation by use of pressures of approximately 300 bar through nozzles with openings measuring approximately 5×8μm.

2. The pharmaceutical preparation according to claim 1, characterised in that it contains 96% (v/v) ethanol as a solvent.

3. A stable pharmaceutical, preparation for use in producing propellant-free aerosols, comprising a steroid and, if necessary, pharmacologically-harmless adjuvants and/or flavourings, characterised in that the pharmaceutical preparation contains at least 85% (v/v) ethanol as a solvent with a pH between 2.0 and 7.0, and if necessary, a complex forming agent wherein the steroid is in an amount of 0.001 to 5.0% by weight.

4. The pharmaceutical preparation according to claim 3, characterised in that the solvent is 96% (v/v) ethanol.

5. The pharmaceutical preparation according to claim 4, characterised in that the complex forming agent is EDTA or a salt thereof.

6. The pharmaceutical preparation according to claim 3, characterised in that the quantity of complex forming agent is between 0.1 and 5 mg/100 ml of solution.

7. The pharmaceutical preparation according to claim 1, characterised in that the pH value of the preparation is adjusted to a level between 3.2 and 4.5.

8. The pharmaceutical preparation according to claims 3, characterised in that the active substance is flunisolide or budesonide.

9. The pharmaceutical preparation according to claim 1, characterised in that the active substance is tiotropium or an acid addition salt thereof.

10. The pharmaceutical preparation according to claim 1, characterised in that the active substance is 3-[(hydroxydi-2-thienylacetyl)oxy]-8,8-dimethyl-8-azoniabicyclo[3,2,1]oct-6-ene or an acid addition salt thereof.

11. A stable pharmaceutical preparation for use in producing a propellant-free metering aerosol containing, per 100 ml of 96% (v/v) ethanol, 1.667 g of flunisolide hemihydrate and 1 mg of disodium EDTA, the pH value of the pharmaceutical preparation being adjusted to 4.0.

12. A stable pharmaceutical preparation for use in producing a propellant-free metering aerosol containing, per 100 ml of 90% (v/v) ethanol, 1.667 g of flunisolide hemihydrate and 1 mg of disodium EDTA, the pH value of the pharmaceutical preparation being adjusted to 4.0.

13. A stable pharmaceutical preparation for use in producing a propellant-free metering aerosol containing, per 100 ml of 96% (v/v) ethanol, 1.333 g of budesonide and 1 mg of disodium EDTA, the pH value of the pharmaceutical preparation being adjusted to 4.0.

14. A stable pharmaceutical preparation for use in producing a propellant-free metering aerosol containing, per 100 ml of 90% (v/v) ethanol, 1.333 g of budesonide and 1 mg of disodium EDTA, the pH value of the pharmaceutical preparation being adjusted to 4.0.

15. A delivery system for a pharmacologically active substance which comprises a stable preparation as defined in claim 1 in combination with a propellant-free nebuliser.

* * * * *